United States Patent [19]

Brown et al.

[11] Patent Number: 5,621,097
[45] Date of Patent: Apr. 15, 1997

[54] OXIDATION OF ORGANOSULPHUR COMPOUNDS

[75] Inventors: Scott W. Brown, Standish; Angela M. Lee, West Derby; Stephen C. Oakes, Widnes, all of United Kingdom

[73] Assignee: Solvay Interox Limited, Barrington, England

[21] Appl. No.: 553,009

[22] Filed: Nov. 3, 1995

[30] Foreign Application Priority Data

Nov. 5, 1994 [GB] United Kingdom .................. 9422391

[51] Int. Cl.$^6$ ................................................ C07D 499/48
[52] U.S. Cl. ............................. 540/342; 562/30; 562/115
[58] Field of Search ............................. 540/342; 562/30, 562/115

[56] References Cited

U.S. PATENT DOCUMENTS 5,286,885  2/1994  Goetz et al. .

FOREIGN PATENT DOCUMENTS 8301909  2/1982  Spain .

OTHER PUBLICATIONS

Ishii et al., "Selectivity in Oxidation of Sulfides with Hydrogen Peroxide by . . . ", Chemistry Letters, pp. 1–4, 1994, The Chemical Society of Japan.
Arcoria et al., "The Relevance of Acid–Based Equilibria in the Catalytic Oxidations by Tungsten and Molybdenum Peroxo Complexes", Journal of Molecular Catalysis, 24 (1984), pp. 189–196.
Chemical Abstract 91:73935x, "Liquid–phase oxidation of alkyl sulfides catalyzed by a heteropoly acid", 22–Physical Org. Chem., vol. 91, 1979, p. 537.
Castello, J.C. et al., "Sistemas cataliticos de oxidacion II: Oxidacion de sulfuros a sulfoxidos . . . ", Afinidad XLIII 406, Nov.–Dec. 1986, pp. 505–507.
Ballistreri et al., "Oxygen Transfer Processes to Sulfides and Sulfoxides Mediated by Cetylpyridinium Tetrakis (diperoxomolybdo) phosphate", Journal of Molecular Catalysis, 68, (1991), pp. 269–275.
Ballistreri et a., "Reactivity of Peroxyopolyoxo Complexes. Oxidation of Thioethers, Alkenes and Sulfoxides by Tetrahexylammonium Tetrakis (diperoxomolybdo) phosphate", J. Org. Chem., 1992, 57, 7074–7077.
Arcoria, et al., J. Mol. Catal., 24, 189–96, 1984.
Castellvi, et al., Afinidad XLIII, 406, 505–07, 1986.
Ballisteri, et al., J. Org. Chem. 57, 7074–77, 1992.
Paolo, et al., J. Mol. Catal., 68, 269–75, 1991.

*Primary Examiner*—Joseph Conrad
*Attorney, Agent, or Firm*—Larson and Taylor

[57] ABSTRACT

A process for the oxidation of organosulphur compounds with hydrogen peroxide is provided. The process employs solid supported polyacids comprising tungsten, molybdenum and/or vanadium as catalysts. The supports are selected from compounds, preferably oxides, of Group IIa, IIb, IIIb, IVa and IVb elements, and strong base ion exchange resins. Certain embodiments of the process provide for the oxidation of sulphides to sulphoxides or sulphones, particularly for the oxidation of penicillins to penicillin sulphoxides. Other embodiments of the process provide for the selective oxidation of thiols to sulphoxides.

18 Claims, No Drawings

OXIDATION OF ORGANOSULPHUR COMPOUNDS

This invention concerns the oxidation of organosulphur compounds.

In the agrochemical and pharmaceutical industries, it is often desired to oxidise sulphur compounds. One particular sulphur oxidation that it is desirable to perform is the oxidation of the sulphide group in penicillins to the corresponding sulphoxide. This is of particular commercial importance as the sulphoxide is often employed as an intermediate in the production of cephalosporins. A further important sulphur oxidation is the oxidation of thiols to sulphonic acids. The oxidation of thiols is not only important in the agrochemical and pharmaceutical industries, but is also of importance in the field of waste treatment, where it is often desirable to oxidise malodorous thiols to relatively odour free compounds.

An aqueous solution of hydrogen peroxide would be a desirable oxidant to employ in the oxidation of sulphur compounds because it is relatively cheap, easy to handle and is environmentally acceptable in that its decomposition products are water and oxygen. Although hydrogen peroxide can oxidise some sulphur compounds to a certain extent in the absence of a catalyst, it has often been found that the use of a catalyst is preferred, in order, for example, to increase the rate of reaction or to favour the production of a particular, desired product. Some catalysts, particularly transition metal-based catalysts such as copper (II), iron (II), tungstate and vanadate, are well known in the sulphur oxidation art. However, many such catalysts are employed as homogeneous catalysts i.e. they are employed in the same phase and/or physical state as the reagents. Additionally, Spanish Patent No. 8301909 describes the use of soluble heteropolyacids as homogeneous catalysts for the oxidation of sulphides to sulphones.

Although the use of homogeneous catalysts normally has the advantage of a relatively high rate of reaction compared with other forms of catalyst, one drawback of such an approach is that the reaction depends on the formation of a solution of the catalyst, which is then brought into contact with the substance to be oxidized. This means that on completion of the reaction, the catalyst often remains in solution. Such a solution can, in theory, be separated from the reaction product and recycled, but in many cases, and particularly where the product is a liquid, this process can involve a distillation stage. It is widely recognised that the distillation of a solution which may contain peroxide residuals is a potentially hazardous operation because the potential concentration of peroxides can result in the formation of explosive compositions. In order to reduce such hazards, solutions which may contain peroxide residuals are often chemically treated, typically with a reducing agent such as sodium thiosulphate solution, to remove any peroxide residuals. Unfortunately, such a chemical treatment can alter the chemical nature of catalyst remaining in solution, particularly in the case of relatively complex catalysts such as heteropolyacids, and this can mean that the activity of the catalyst is lost or significantly reduced when the solution is recycled, thereby rendering its recycling ineffective.

An alternative to recycling is to dispose of such solutions to waste, but such disposal is becoming increasingly restricted by regulation and correspondingly more expensive. In addition, such a disposal also represents a significant chemical cost because of the loss of chemicals, and particularly for relatively expensive transition metals. It has therefore become expedient to recover spent catalyst if possible, notwithstanding the problems outlined hereinbefore, but where the catalyst is in solution, such recovery can involve the construction and operation of relatively expensive separation plants. It is therefore desirable to identify a process for the oxidation of organosulphur compounds with hydrogen peroxide that employs a catalyst that can be relatively easily separated from the reaction medium.

In an alternative method to improve recovery and recycle of the catalyst from a reaction mixture, one approach that can be contemplated at least in theory, is to employ a heterogeneous catalyst. As the majority of reaction systems employed are liquid, such heterogeneous catalysts are most commonly solids. However, if a catalyst is present in a different physical form to the reagents, the extent of intimate contact between them is reduced, and this can result in the rate of reaction being unacceptably slow, or even in there being no detectable reaction. It is therefore desirable that the heterogeneous catalyst employed does not result in an unacceptably slow reaction. U.S. Pat. No. 5,286,885 discloses certain polymeric organosiloxane ammonium salts, including polyacid salts. It is asserted that these salts can function as heterogeneous catalysts for a very wide range of oxidation reactions, including the oxidation of thiols. There is no disclosure of the use of an inorganic oxide support for polyacid salts. Additionally, the use of polyacid charged ion exchange resins as heterogeneous catalysts is taught to be unsatisfactory. The general teaching of U.S. Pat. No. 5,286,885 notwithstanding, it remains desirable to identify additional or further heterogeneously catalysed oxidation processes for sulphur compounds.

Accordingly, it is an object of the present invention to provide an additional or further catalysed process for the oxidation of oxidisable organosulphur compounds with hydrogen peroxide in the presence of a catalyst that can be separated relatively easily from the reaction medium.

It is another object of the present invention in at least some embodiments to provide an additional or further process for the oxidation of oxidisable organosulphur compounds with hydrogen peroxide in the presence of a heterogeneous catalyst that can be separated relatively easily from the reaction medium that does not result in an unacceptably slow reaction.

It is a further object of certain other embodiments of the present invention to provide a process for the oxidation of thiols giving improved selectivity to sulphonic acids.

It is an object of yet other embodiments of the present invention to provide a process for the oxidation of sulphides to sulphoxides or sulphones with hydrogen peroxide in the presence of a catalyst that can be separated relatively easily from the reaction medium.

According to the present invention, there is provided a process for oxidation of oxidisable organosulphur compounds, wherein a substrate organosulphur compound is contacted with hydrogen peroxide in a reaction medium in the presence of a solid supported polyacid catalyst, characterised in that the polyacid comprises one or more of tungsten, molybdenum and vanadium, and the support is selected from the group consisting of:

a) compounds of Group IIa, IIb, IIIb, IVa and IVb elements, and b) strong base ion exchange resins.

According to certain embodiments of the present invention, there is provided a process for the oxidation of sulphides to sulphoxides or sulphones wherein a substrate sulphide is contacted with hydrogen peroxide in a reaction medium in the presence of catalyst, characterised in that the catalyst comprises a solid supported polyacid comprising one or more of tungsten, molybdenum and vanadium, the support being selected from the group consisting of:

a) compounds of Group IIa, IIb, IIIb, IVa and IVb elements, and b) strong base ion exchange resins.

According to other embodiments of the present invention, there is provided a process for the selective oxidation of thiols to sulphonic acids wherein a substrate thiol is contacted with hydrogen peroxide in a reaction medium in the presence of catalyst, characterised in that the catalyst comprises a solid supported polyacid comprising one or more of tungsten, molybdenum and vanadium, the support being selected from the group consisting of:

a) compounds of Group IIa, IIb, IIIb, IVa and IVb elements, and b) strong base ion exchange resins.

For the avoidance of doubt, the division herein of the Elements of the Periodic Table into Groups a and b is that employed by F A Cotton and G Wilkinson in Advanced Inorganic Chemistry (2nd Edition) published by Interscience (John Wiley and Sons).

In the process according to the present invention, the catalyst comprises a polyacid comprising one or more of tungsten, molybdenum and vanadium. It will be recognised that the polyacid can be present as in free acid form or in salt form. The polyacid may be a heteropolyacid or an isopolyacid. When the catalyst is a heteropolyacid, the catalyst contains a non-metallic heteroatom which may be selected from Group IV including silicon and germanium or Group V including phosphorus. Preferably, when a heteropolyacid catalyst is employed, the catalyst contains phosphorus as the non-metallic heteroatom.

Tungsten, molybdenum or vanadium can constitute the entire metallic component of the heteropolyacid, or at least one other transition metal can be incorporated therein.

Certain vanadium-free heteropolyacids for employment in the present invention process can be represented by the general chemical formula $Q_{3/n}XMo_wW_zO_{40}$ when they are brought into contact with the support in which w and z represent zero or a positive integer such that w+z=12. Q represents hydrogen or like counterion, and n is its basicity in the general formula, and X represents P or Si.

Other vanadium-free heteropolyacids that can be employed in the present invention include those containing at least one first series transition metal, including specifically iron, manganese, cobalt and nickel, for example in heteropolyacids of the formula $Q_{(7-t)/n}PM_{11}ZO_{39}$ in which M represents molybdenum or tungsten, Z represents the first row transition metal, t is its oxidation state and Q is the counterion of basicity n as before.

Vanadium-containing heteropolyacids that can be employed in the process according to the present invention include those which can be represented by the general chemical formula $Q_{3+v}PM_nV_vO_{40}$ in which M represents molybdenum or tungsten, v is from 1 to 3, n is a positive integer such that n+v=12 and Q is the counterion. Other vanadium containing heteropolyacids can be represented by the general chemical formula $Q_8HPV_{14}O_{42}$, where Q is a univalent counter ion.

Isopolyacids that can be employed in the process according to the present invention can be represented by the general chemical formula $Q_x(M_mO_y)$ where M represents molybdenum, tungsten or vanadium in its highest oxidation states, Q is a counter ion, m is 2 or more, commonly from 4 to 30, most commonly from 5 to 20, with y and x being positive integers to satisfy valency and charge requirements. Particular examples include those comprising ions having the general chemical formulae $[M_6O_{19}]^{2-}$, $[M_7O_{24}]^{6-}$, $[M_9O_{32}]^{10-}$, $[M_{10}O_{32}]^{4-}$, $[M_{18}O_{62}]^{6-}$, where M represents Mo or W, and those comprising ions having the general formulae $[V_3O_9]^{3-}$, $[V_4O_{12}]^{4-}$, and $[V_{10}O_{28}]^{6-}$. In some embodiments of the present invention, good results have been achieved employing an isopolyacid comprising $[Mo_7O_{24}]^{6-}$ ions.

The support for the heteropolyacid catalyst is selected from solid compounds of Group IIa, IIb, IIIb, IVa and IVb elements, preferably oxides, and from organic basic ion exchange resins. Within the class of Group IIa compounds, it is often convenient to select from magnesium compounds, including in particular magnesium oxide and magnesium silicate. Within the class of group IIb compounds, it can be convenient to select from zinc compounds as support, including specifically zinc oxide. Within the class of Group IVa compounds, it is often convenient to select from titanium or zirconium compounds, including specifically titanium oxide and zirconium phosphate. From within the class of inorganic Group IVb compounds, it is often desirable to select as supports from silicates, tin compounds, many of which are readily available, or from germanium compounds. Specific examples include tin oxide.

In a number of preferred embodiments, the catalyst support is selected from Group IIIb compounds, especially from non-sintered oxides, and particularly from aluminium oxides. An especially suitable support comprises an activated alumina, including in particular, gamma alumina. For the avoidance of doubt, the term activated alumina refers to non-sintered alumina obtainable by calcining alumina or aluminium hydroxide at a temperature below that at which sintering occurs, and includes specifically the products obtained by calcining at around 400° to 600° C. The alumina may already be present in the activated form at the time of contact with the catalyst or alternatively neutral alumina or aluminium hydroxide may be converted into activated alumina by a post-impregnation calcination step.

Organic supports that can be contemplated for use in the process of the present invention are selected from strong base ion exchange resins. Such resins typically comprise a cross-linked polystyrene, the cross linking monomer often comprising divinylbenzene in a small fraction of the monomer mix such as 1 to 2 mole %, the benzene nucleus in the styrene being substituted by an organic base, particularly by an alkyleneammonium group. Examples of possible ammonium groups include alkylenetriailkylammonium, often methylenetrimethyl-ammonium or the corresponding groups in which one or more of the methyl groups are replaced by another short chain alkyl such as ethyl and/or one of the alkyl groups being hydroxyl-substituted, as in methylenedimethylhydroxyethylammonium group. Other suitable anion exchange resins include insoluble polyacrylic resins in which the carboxylic acid function is further substituted by an alkyleneammonium group, for example ethylenetrimethylammonium. The ion-exchange resin can be selected from micro or macro-reticulated strongly basic resins. Naturally, the invention does not encompass so calcining any organic resin after impregnation with the heteropolyacid solution that it is structurally harmed.

The support is usually employed in the form of discrete particles, the particle size range often being selected such that the supported catalyst particles are distributed through the reaction mixture to a substantial extent during the agitation of the mixture. A convenient average particle size often lies in the range of from about 100 microns to about 5 mm.

The catalyst can be introduced to the support most conveniently in solution in a suitable solvent, which can comprise water or a polar organic solvent such as a low molecular weight aliphatic alcohol or a mixture thereof. Low molecular weight herein indicates up to C4 (butanols). The solution can, in principle, contain any concentration of catalyst up to and including a saturated solution, and in preference is at or near saturation, so as to minimise the volume of solvent that is subsequently removed. The solution can be contacted with the support in bulk until a desired amount has been absorbed and after separation from the liquid phase, the impregnated support is thereafter dried and can then be calcined. Calcination is an optional, though preferred stage for inorganic supports if an impregnation stage is employed. The impregnation contact period often lasts from about 30 minutes to 8 hours. In a variation, the support may be charged into a column through which a solution of the heteropolyacid is permitted to percolate, preferably with recycle of the eluate to maximise uptake of the catalyst from the solvent.

The contact may be made at or around ambient temperature, which is typically in the region of from about 15° to 25° C. or it may be conducted at an elevated temperature up to the boiling point of the solvent under the selected pressure conditions. By employing an elevated temperature, and particularly one that is within 10° C. of the solvent boiling point, the solvent is evaporated away to at least some extent during the contact period. Once the solution has reached saturation, any further solvent removal results in the catalyst being deposited on the support. Accordingly, the support can thereby be loaded with a higher level of catalyst than is obtainable by simply impregnating the support with a saturated solution, separating the support from excess liquor and drying. Particularly for use in conjunction with solvent evaporation during the contact phase, the solvent is methanol or an alternative low boiling point solvent.

The extent of loading of the catalyst is to at least some extent at the discretion of the user. It is often convenient or desirable to employ a loading of from about 4 to 30% by weight of the catalyst, calculated as the metal, based on the dry weight of the support. In a number of effective embodiments the catalyst loading is between 5 and 17% by weight of the dry weight of the support.

During calcination of the supported catalyst material which has been obtained by impregnation of an inorganic support with the heteropolyacid, it is believed that formation of a bond between the catalyst and the support is promoted, which can assist in controlling the leaching of catalyst into the reaction mixture. However, as a result of such interaction and bond formation, the catalyst species may be altered to some extent by such calcination, so that the value of such a post impregnation calcination tends to vary depending upon the support employed. For some supports, including alumina in particular, it is advantageous to calcine at a temperature of at least 300° C. and usually not higher than about 600° C. In a number of instances, a particularly suitable temperature for post-impregnation calcination of for example alumina is at least about 400° C. and especially from about 450° to about 550° C. Other supports for which post impregnation calcination is an appropriate activity include magnesium silicate and zirconium phosphate. However, when magnesium oxide or a related oxide such as calcium or zinc is employed as support, it can be preferable not to calcine the support after it has been impregnated by the heteropolyacid catalyst.

When the catalyst comprises a mixture of one or more transition metals and/or heteroatoms, it is believed that the supported catalyst retains its empirical ratio of transition metal(s) and/or heteroatom components, but that the interaction of the catalyst with the surface of the support, particularly a support chosen from solid compounds of Group IIa, IIb, IIIb, IVa and IVb elements, may result in the catalyst becoming bonded chemically to the support, thereby modifying both the catalyst itself and the support surface. Such treatments may also encourage a redistribution of transition metal(s) between species of different nuclearity.

The oxidisable organosulphur compounds that can be oxidised by the process according to the present invention comprise a very wide group of chemicals. Oxidisable organosulphur compounds comprise at least one sulphur atom which is in an oxidation state of less than 6, and most commonly at least one sulphur atom in an oxidation state of 2 or 4. The group includes primary, secondary and tertiary, linear, branched and cyclic aliphatic and aromatic thiols, sulphides and sulphoxides. It will be recognised that in such a wide group, certain members of the group will be rather more readily oxidisable than others, in accordance with well established chemical principles. It will also be recognised that on account of the chemistry of many organosulphur compounds, the oxidation of organosulphur compounds with hydrogen peroxide often proceeds via a number of intermediate oxidised products representing increased oxidation of the sulphur group. In many instances, the reaction conditions employed, for example, mole ratio of hydrogen peroxide to substrate sulpho group and reaction temperature, can be controlled to favour a particular oxidation product, particularly in the case where the desired product is susceptible of further oxidation. An example of this is the oxidation of mercaptans, which is believed to be oxidised first to a disulphide, then subsequently to a thiosulphinate, thiosulphonate, disulphone and finally dismutates to a sulphonic acid. Similarly, sulphides can be oxidised to sulphoxides, which can in turn be oxidised to sulphones.

Examples of aliphatic thiolsthat can be oxidised by the process according to the present invention include mercaptans such as methyl, ethyl, propyl, iso-propyl, dodecyl and cyclohexyl mercaptan, Examples of aromatic thiolsthat can be oxidised by the process according to the present invention include thiophenol, substituted thiophenols and thionaphthol and substituted thionaphthols. Examples of sulphides that can be oxidised by the process according to the present invention include alkyl and aryl disulphides such as dimethyl sulphide and diphenyl sulphide, particularly substituted aromatic sulphoxides such as bis(4-aminophenyl)sulphide. One particularly important group of sulphides are cyclic sulphides where the sulphur atom comprises part of the ring structure, especially pharmacologically important examples such as the penicillins. Particularly preferred sulphides comprise penicillin-G and penicillin-V, and salts thereof. Examples of sulphoxides that can be oxidised by the process according to the present invention include particularly substituted aromatic sulphoxides such as bis(4-aminophenyl)sulphoxide.

Where the substrate organosulphur compound is liquid at the reaction temperature, the substrate can serve as its own solvent, thus avoiding the need for the use of an additional component and reducing the process costs. However, in many embodiments it is desirable to employ an additional solvent.

In most embodiments of the present invention where an additional solvent is employed, the solvent is resistant to oxidation, by which is meant that under the conditions employed, the solvent is either not oxidised at all, or is oxidised at such a slow rate that substantially no oxidation of the solvent occurs during the reaction time employed. It will be recognised, however, that it can be desirable to employ a solvent that is less resistant to oxidation if the use of such a solvent is necessary to achieve a particular effect, for example to solubilise a particular reagent. In such cases, it is preferable that the solvent has a relatively low rate of oxidation compared to the substrate. The actual solvent chosen will depend upon the nature and solubility of the substrate organosulphur compound. In many embodiments of the present invention, the solvent is chosen from water and water-miscible solvents including low molecular weight alcohols such as methanol, ethanol, propan-1-ol, propan-2-ol and tertiary butanol, low molecular weight carboxylic acids such as acetic acid and propionic acid, and nitriles such as acetonitrile, with tertiary butanol and acetonitrile being preferred. It will be recognised, however, that the use of a carboxyl-containing solvent can result in the in-situ formation of a peracid, and that in certain cases where the substrate contains a group which is sensitive to oxidation by a peracid, such as a carbon-carbon double bond, it can be desirable to employ a noncarboxyl containing solvent.

Although the additional solvent is preferably water or miscible with water, water immiscible solvents may be employed, but it is believed that the use of a phase transfer catalyst, which would be advantageous to achieve an efficient process, would tend to result in the leaching of the catalyst off the support, which would reduce the desirability of the process. Water immiscible solvents that can be contemplated for use in the process according to the present invention include halogenated solvents such as dichloromethane, chloroform, carbon tetrachloride and 1,2-dichloroethane. When an additional solvent is employed, the weight ratio of solvent to organosulphur compound is commonly selected in the range of from 1:1 to 50:1, often from 5:1 to 20:1.

The process according to the present invention is carried out at a temperature selected depending upon the nature of the substrate and the particular oxidation product it is desired to produce. For example, when the substrate is a thiol and it is desired to produce a sulphonic acid, an elevated temperature is commonly employed, typically from 50° C. up to the reflux temperature of the reaction medium, and particularly from 60° to 85° C. In some embodiments of the present invention, however, and particularly when the substrate is a penicillin and it is desired to produce a sulphoxide, much lower temperatures such as ambient, for example, 15° to 25° C. or sub-ambient temperatures, such as down to about −15° C. can be employed. The use of such lower temperatures may be particularly desirable when the substrate comprises other functional groups than the sulphur group which may be sensitive to oxidation with hydrogen peroxide at higher temperatures.

Hydrogen peroxide can be introduced into the reaction mixture in an amount which is stoichiometric, sub-stoichiometric or greater than stoichiometric for the desired oxidation, based on the mole ratio of hydrogen peroxide to substrate sulpho group. It may be preferable to employ a sub-stoichiometric amount of hydrogen peroxide when the substrate is particularly sensitive to further oxidation, particularly if the unreacted substrate can readily be recycled. When the substrate comprises a thiol and it is desired to produce a sulphonic acid, it is preferred to employ at least a stoichiometric amount of hydrogen peroxide, and often an excess of hydrogen peroxide, such as up to 6 moles of hydrogen peroxide per mole of oxidisable thiol, i.e. 2 times stoichiometric, and preferably from about 3 to about 5 moles of hydrogen peroxide per mole of oxidisable thiol, i.e. about stoichiometric to about 1.7 times stoichiometric. When the substrate comprises a sulphide, the mole ratio of hydrogen peroxide to substrate sulpho group is normally about 1:1 when it is desired to produce a sulphoxide, and about 2:1 when it is desired to produce a sulphone.

The hydrogen peroxide is preferably introduced into the reaction mixture in the form of a concentrated aqueous solution, and frequently of from about 30 to 70% w/w hydrogen peroxide. Preferably, the hydrogen peroxide is introduced into the reaction mixture which contains both the substrate and catalyst system, and particularly preferably it is introduced gradually, for example over a period of from 15 minutes to 4 hours, such as in small increments or in a continuous feed.

The ratio of supported catalyst to substrate can be selected over a wide range of weight ratios, often in the range of from 1:1 to 1:50 and in a number of instances from 1:5 to 1:25. The ratio chosen can take into account the loading of catalyst on the support and the activity of the substrate, as well as the other reaction conditions selected.

The overall reaction period, including the period of introduction of the second reagent which is normally hydrogen peroxide, often comprises from about 2 to about 12 hours, and in many instances is from about 3 to about 8 hours. However, longer reaction periods of for example 12 to 30 hours can be employed, if desired by the user.

When the oxidation process has been permitted to continue for the desired period, the reaction can be halted by physically separating the particulate catalyst from the reaction mixture by filtration or centrifugation and/or by cooling the mixture for example to ambient. The recovered catalyst can be re-employed in a further reaction mixture, possibly after washing with solvent and/or drying and/or re-calcination, if desired.

According to one preferred aspect of the present invention, there is provided a process for the oxidation of penicillins to penicillin sulphoxides wherein a substrate penicillin is contacted with hydrogen peroxide in a reaction medium in the presence of supported catalyst, characterised in that the catalyst comprises $[Mo_7O_{24}]^{6-}$ or $H_3PW_{12}O_{40}$, the support comprises gamma alumina or a cross-linked polystyrene strong base ion exchange resins, and that the process is effected at a temperature of from 15° to 25° C.

According to a second preferred embodiment of the present invention, there is provided a process for the selective oxidation of thiols to sulphonic acids wherein a substrate thiol is contacted with hydrogen peroxide in a reaction medium in the presence of catalyst, characterised in that the catalyst comprises a polyacid supported on gamma alumina, the polyacid having the general chemical formula $Q_{3/n}PMo_wW_zO_{40}$ when the polyacid is brought into contact with the support, in which w and z represent zero or an integer such that w+z=12, Q represents hydrogen or like counterion, and n is its basicity in the general formula and that the process is effected at a temperature of from 60° to 85° C.

Having described the invention in general terms, specific embodiments thereof are described in greater detail by way of example only.

Catalyst Preparation Method A—Inorganic support 3 g of the selected polyacid was dissolved in 25 ml of demineralised water. To this solution was added 20 g of the selected support, and the mixture stirred at room temperature for 4 hours. The slurry was filtered, and the residue dried in an oven at 60° C. overnight. The dried solid was then calcined at 500° C. for 4 hours in a muffle furnace. The catalysts produced had a nominal polyacid loading of 10%.

Catalyst preparation Method B—Organic support $(NH_4)_6Mo_7O_{24}$ was supported on a cross-linked polystyrene strongly basic anion exchange resin in chloride form ($A_{26}$ Beads, commercially available in the UK from BDH Chemicals Ltd, 1.7 meq/ml Cl⁻) by stirring 2.3 cm³ of A26 beads in a solution comprising $(NH_4)_6Mo_7O_{24}$ (2.1 g) dissolved in 20 g of demineralised water at room temperature for 2 hours. The resin was then filtered off, washed with demineralised water (2×50 cm³ aliquots), washed with acetone, and then dried under vacuum at 50° C. for 2 hours.

EXAMPLE 1

Thiophenol (4 g, 36.4 mmol), t-butanol (40 ml) and $H_3PW_{12}O_{40}$/gamma $Al_2O_3$ prepared by Method A above (0.5 g) were charged into a reaction vessel and heated to 80° C. with stirring. Aqueous 35% w/w hydrogen peroxide (7.1 g, 72.7 mmol) was added over 45 minutes whilst maintaining stirring and the temperature was maintained at 80° C. On completion of the hydrogen peroxide addition, the reaction was maintained under these conditions for a further 4 hours.

Analysis of the reaction mixture by gas chromatography showed that 100% of the thiophenol had been converted, with a selectivity to benzenesulphonic acid of 94%.

EXAMPLE 2

The procedure of Example 1 was followed, except that $H_4SiW_{12}O_{40}$ supported on gamma $Al_2O_3$ prepared by Method A (0.5 g) was employed as catalyst.

100% of thiophenol was converted, with a selectivity to benzenesulphonic acid of 69%.

Comparison 3

The procedure of Example 1 was followed, except that no catalyst was employed.

The conversion of thiophenol was again 100%, but the selectivity to benzenesulphonic acid was only 42%.

EXAMPLE 4

Penicillin-G, potassium salt (4 g, 10.8 mmol), water (40 ml) and the catalyst prepared by Method B above (0.5 g) were charged into a reaction vessel at room temperature (ca 20° C.). Aqueous 35% w/w hydrogen peroxide (1.04 g, 10.8 mmol) was added over 45 minutes with stirring and the temperature was maintained at room temperature. On completion of the hydrogen peroxide addition, the reaction was maintained under these conditions for a further 4 hours.

Analysis of the reaction mixture by gas chromatography showed that 96% of the penicillin-G had been converted, giving a yield of the sulphoxide of 75%, a selectivity of 78%.

EXAMPLE 5

The procedure of Example 4 was followed, except that $H_4PMo_{11}VO_{40}$ supported on gamma alumina prepared by Method A above was employed as catalyst.

Analysis of the reaction mixture by gas chromatography showed that 34% of the penicillin-G had been converted, giving a yield of the sulphoxide of 69%, a selectivity of 49.3%.

EXAMPLE 6

The procedure of Example 5 was followed, except that the reaction was carried out at −10° C. in isopropanol/water (1:1 w/w) as solvent.

Analysis of the reaction mixture by gas chromatography showed that 31% of the penicillin-G had been converted, giving a yield of the sulphoxide of 21.8%, a selectivity of 70.3%.

EXAMPLE 7

The procedure of Example 6 was followed, except that $H_3PW_{12}O_{40}$ supported on gamma alumina prepared by Method A above was employed as catalyst.

Analysis of the reaction mixture by gas chromatography showed that 74.4% of the penicillin-G had been converted, giving a yield of the sulphoxide of 48.3%, a selectivity of 65%.

EXAMPLE 8

The procedure of Example 7 was followed, except that the reaction was carried out at room temperature (ca. 20° C.) in water as solvent. Subsequently, the reaction mixture was stored at 2° C. for 3 days before analysis.

Analysis of the reaction mixture by gas chromatography showed that 96% of the penicillin-G had been converted, giving a yield of the sulphoxide of 72.5%, a selectivity of 75.3%.

Comparison 9

The procedure of Example 4 was followed, except that no catalyst was employed.

Analysis of the reaction mixture by gas chromatography showed that only 12% of the penicillin-G had been converted, giving a yield of the sulphoxide of only 9.6%.

The results of Examples 1 and 2 showed that the process according to the present invention gave significantly superior selectivity in the oxidation of thiophenol to benzenesulphonic acid compared with the similar non-catalysed process of Comparison 3, where a much lower selectivity was achieved. The result of Example 1 further showed that a particularly favourable and selective conversion of thiol to sulphonic acid was achieved when phosphorus was present in the heteropolyacid. The results of Examples 4 to 8 showed that sulphides could successfully be oxidised to sulphoxides by the process according to the present invention, and that, particularly in the case of the oxidation of penicillin-G, excellent results could be obtained by the use of supported $(NH_4)_6Mo_7O_{24}$ as catalyst. The results of Examples 6 and 7 showed that temperatures as low as −10° C. could successfully be employed. The result of Comparison 9 showed that when no catalyst is employed, the conversion of sulphoxide and yield were extremely low.

We claim:

1. In a process for oxidation of oxidisable organosulphur compounds, wherein a substrate organosulphur compound is contacted with hydrogen peroxide in a reaction medium in the presence of a solid supported polyacid catalyst, the improvement wherein the polyacid comprises one or more of tungsten, molybdenum and vanadium, and the support is selected from the group consisting of:

a) compounds of Group IIa, IIb, IIIb, IVa and IVb elements, and b) strong base ion exchange resins.

2. In a process for the oxidation of sulphides to sulphoxides or sulphones wherein a substrate sulphide is contacted with hydrogen peroxide in a reaction medium in the presence of catalyst, the improvement wherein the catalyst comprises a solid supported polyacid comprising one or more of tungsten, molybdenum and vanadium, the support being selected from the group consisting of:

a) compounds of Group IIa, IIb, IIIb, IVa and IVb elements, and b) strong base ion exchange resins.

3. In a process for the selective oxidation of thiols to sulphonic acids wherein a substrate thiol is contacted with hydrogen peroxide in a reaction medium in the presence of catalyst, the improvement wherein the catalyst comprises a solid supported polyacid comprising one or more of tungsten, molybdenum and vanadium, the support being selected from the group consisting of:

a) compounds of Group IIa, IIb, IIIb, IVa and IVb elements, and b) strong base ion exchange resins.

4. A process according to claim 1, 2 or 3, wherein the supported polyacid has the general chemical formula $Q_{3/n}X\text{-}Mo_wW_zO_{40}$ when brought into contact with the support in which w and z represent zero or a positive integer such that w+z=12, Q represents hydrogen or like counterion, and n is its basicity in the general formula, and X represents P or Si.

5. A process according to claim 4, wherein the supported polyacid has the general chemical formula $H_3PW_{12}O_{40}$.

6. A process according to claim 1, 2 or 3, wherein the supported polyacid has the general chemical formula $Q_{3+v}PM_nV_vO_{40}$ in which M represents molybdenum or tungsten, v is from 1 to 3, n is a positive integer such that n+v=12 and Q is the counterion.

7. A process according to claim 1, 2 or 3, wherein the supported polyacid has the general chemical formula $Q_x(M_mO_y)$ where M represents molybdenum, tungsten or vanadium in its highest oxidation states, Q is a counter ion, m is 2 or more, with y and x being positive integers to satisfy valency and charge requirements.

8. A process according to claim 7, wherein the supported polyacid comprises $[Mo_7O_{24}]^{6-}$ ions.

9. A process according to claim 7 wherein M is from 4 to 30.

10. A process according to claim 7 wherein M is from 5 to 20.

11. A process according to claim 1, 2 or 3, wherein the support comprises gamma alumina or a cross-linked polystyrene strong base ion exchange resins.

12. A process according to claim 11, wherein the supported polyacid has the chemical formula $H_3PW_{12}O_{40}$ or comprises $[Mo_7O_{24}]^{6-}$ ions.

13. A process according to claim 1, 2 or 3, wherein the support is selected from Group IIa, IIb, IIIb, IVa and IVb oxides.

14. A process according to claim 13, wherein the supported polyacid has the chemical formula $H_3PW_{12}O_{40}$ or comprises $[Mo_7O_{24}]^{6-}$ ions.

15. In a process for the selective oxidation of thiols to sulphonic acids wherein a substrate thiol is contacted with hydrogen peroxide in a reaction medium in the presence of catalyst, the improvement wherein the catalyst comprises a polyacid supported on gamma alumina, the polyacid having the general chemical formula $Q_{3/n}PMo_wW_zO_{40}$ when the polyacid is brought into contact with the support, in which w and z represent zero or an integer such that w+z=12, Q represents hydrogen or like counterion, and n is its basicity in the general formula and that the process is effected at a temperature of from 60° to 85° C.

16. In a process for the oxidation of penicillins to penicillin sulphoxides wherein a substrate penicillin is contacted with hydrogen peroxide in a reaction medium in the presence of supported catalyst, the improvement wherein the catalyst comprises $[Mo_7O_{24}]^{6-}$ or $H_3PW_{12}O_{40}$, the support comprises gamma alumina or a cross-linked polystyrene strong base ion exchange resin, and that the process is effected at a temperature of from 15° to 25° C.

17. A process according to either of claims 2 or 16, wherein the substrate is penicillin-G.

18. A process according any one of claims 1, 2, 3, 15 or 16, wherein the reaction medium additionally comprises water and/or a water miscible organic solvent.

* * * * *